United States Patent
Ghosh et al.

(10) Patent No.: US 8,956,836 B2
(45) Date of Patent: Feb. 17, 2015

(54) **INTEGRATED PROCESS FOR THE PRODUCTION OF *JATROPHA* METHYL ESTER AND BY PRODUCTS**

(75) Inventors: Pushpito Kumar Ghosh, Bhavnagar (IN); Sandhya Chandrika Prasad Mishra, Bhavnagar (IN); Mahesh Ramniklal Gandhi, Bhavnagar (IN); Sumesh Chandra Upadhyay, Bhavnagar (IN); Parimal Paul, Bhavnagar (IN); Pritpal Singh Anand, Bhavnagar (IN); Kiritkumar Mangaldas Popat, Bhavnagar (IN); Anupama Vijaykumar Shrivastav, Bhavnagar (IN); Sanjiv Kumar Mishra, Bhavnagar (IN); Neelam Ondhiya, Bhavnagar (IN); Ramesh Dudabhai Maru, Bhavnagar (IN); Gangadharan Dyal, Bhavnagar (IN); Harshad Brahmbhatt, Bhavnagar (IN); Vinod Boricha, Bhavnagar (IN); Doongar Ram Chaudhary, Bhavnagar (IN); Babulal Rebary, Bhavnagar (IN); Krushnadevsingh Sukhdevsinh Zala, Bhavnagar (IN)

(73) Assignee: Council of Scientific and Industrial Research, New Delhi (IN)

( * ) Notice: Subject to any disclaimer, the term of this patent is extended or adjusted under 35 U.S.C. 154(b) by 366 days.

(21) Appl. No.: 13/981,742

(22) PCT Filed: Mar. 29, 2010

(86) PCT No.: PCT/IN2010/000192
§ 371 (c)(1),
(2), (4) Date: Oct. 10, 2013

(87) PCT Pub. No.: WO2011/027353
PCT Pub. Date: Mar. 10, 2011

(65) Prior Publication Data
US 2014/0038249 A1    Feb. 6, 2014

(30) Foreign Application Priority Data
Sep. 7, 2009   (IN) .......................... 1838/DEL/2009

(51) Int. Cl.
*C10L 1/02*      (2006.01)
*C11C 1/08*      (2006.01)
(Continued)

(52) U.S. Cl.
CPC . *C11C 3/06* (2013.01); *C10L 1/026* (2013.01); *C11C 1/08* (2013.01); *C11C 3/003* (2013.01); *C12P 7/625* (2013.01); *Y02E 50/13* (2013.01); *C10G 2300/1014* (2013.01)
USPC ......................................... 435/135

(58) Field of Classification Search
CPC .......... C10L 1/1802; C10L 2200/0476; C10L 2200/0484; C10L 2200/0469; C10L 2290/10; C10L 2290/12; C10L 2290/545; C10L 5/445; C10L 5/02; C11C 3/003; C11B 1/06; C11B 1/10; B30B 11/00; A23N 5/00–5/08; C12P 7/625
See application file for complete search history.

(56) References Cited

U.S. PATENT DOCUMENTS 504,244 A * 8/1893 Read .............................. 99/570
5,424,467 A * 6/1995 Bam et al. ...................... 554/216
(Continued)

FOREIGN PATENT DOCUMENTS

WO   2006/043281 A1   4/2006
WO   2008/120223 A1   10/2008

OTHER PUBLICATIONS

Ashwani Kumar, Satyawati Sharma, An evaluation of multipurpose oil seed crop for industrial uses (*Jatropha curcas* L.): A review, 2008, Industrial Crops and Products, vol. 28, pp. 1-10.*
(Continued)

*Primary Examiner* — Blaine Lankford
*Assistant Examiner* — Trent R Clarke
(74) *Attorney, Agent, or Firm* — Ladas & Parry LLP

(57) ABSTRACT

The present invention provides a simpler and more energy efficient process for the preparation of fatty acid methyl ester (biodiesel) from sun dried whole seed capsules of *Jatropha curcas* integrated with value addition of seed shells, deoiled cake and crude glycerol co-product stream. More specifically, the invention relates to a method of dispensing with the need for excess methanol recovery through distillation, cost-effective resin treatment for the refining of methyl ester and utilization of co-streams for preparation of high density energy briquettes and Polyhydroxyalkanoate biodegradable polymer in efficient and cost-effective manner.

12 Claims, 7 Drawing Sheets

(51) Int. Cl.
*C11C 3/00* (2006.01)
*C11C 3/06* (2006.01)
*C12P 7/62* (2006.01)

(56) References Cited

U.S. PATENT DOCUMENTS

| | | | |
|---|---|---|---|
| 6,174,501 B1* | 1/2001 | Noureddini | 422/618 |
| 2004/0000522 A1* | 1/2004 | Xie et al. | 210/656 |
| 2006/0080891 A1 | 4/2006 | Ghosh et al. | |
| 2009/0148920 A1* | 6/2009 | Schreck | 435/135 |

OTHER PUBLICATIONS

NPL pdf document"Amberlyst-15 datasheet" downloaded from http://www.dow.com/assets/attachments/business/process_chemicals/amberlyst/amberlyst_15wet/tds/amberlyst_15wet.pdf accessed Apr. 9, 2014.*

P.D. Grover & S.K. Mishra, Biomass Briquetting: Technology and Practices, 1996, Regional Wood Energy Development Programme in Asia, GCP/RAS/154/NET, Field Document No. 46, Food and Agriculture Organization of the United Nations, Bangkok, Apr. 1996, pp. i-43.*

R.N. Singh, D.K. Vyas, N.S.L. Srivastava, Madhuri Narra, SPRERI experience on holistic approach to utilize all parts of *Jatropha curcas* fruit for energy, 2008, Renewable Energy, vol. 33, pp. 1868-1873.*

Martin Koller, Rodolfo Bona, Gerhart Braunegg, Carmen Hermann, Predrag Horvat, Markus Kroutil, Julia Martinz, Jose Neto, Luis Pereira, and Paula Varila, Production of Polyhydroxyalkanoates from Agricultural Waste and Surplus Materials, 2005, Biomacromolecules, vol. 6, pp. 561-565.*

Pathama Chatakanonda, Klanarong Sriroth, Laurent Vaysse and Siriluk Liangprayoon, Fatty acid composition and properties of *Jatropha* seed oil and its methyl ester, 2005, Kasetsart J., vol. 39, pp. 141-146, accessed from Kasetsart University at http://kucon.lib.ku.ac.th/Fulltext/KC4306039.pdf, published on the web Dec. 22, 2007.*

NPL document "*Jatropha*-Handbook_Chapter-3" accessed from http://www.fibronot.nl/download/Jatropha-Handbook_Chapter-3.pdf on Jul. 2, 2014 published on the web Nov. 15, 2008.*

International Search Report dated Sep. 15, 2010 for Application No. PCT/IN2010/000192.

Berchmans, Hanny Johanes, et al., "Biodiesel production from crude *Jatropha curcas* L. seed oil with a high content of free fatty acids", Biosource Technology 99 (2008), pp. 1716-1721.

Banerjee T., et al., Process optimization of catalyst removal and characterization of waste water after alkali-catalyzed transesterification of *Jatropha* oil, International Journal of Green Energy 2009, abstract.

* cited by examiner

INTEGRATED PROCESS FOR THE PRODUCTION OF *JATROPHA* METHYL ESTER AND BY PRODUCTS

RELATED APPLICATION INFORMATION

This application is a 371 of International Application PCT/IN2010/000192 filed 29 Mar. 2010 entitled "Integrated Process For The Production Of *Jatropha* Methyl Ester And By Products", which was published in the English language on 10 Mar. 2011 with International Publication Number WO 2011/027353 A1 and which claims priority from Indian Patent Application 1838/DEL/2009, filed 7 Sep. 2009, the content of which are incorporated herein by reference.

FIELD OF THE INVENTION

The present invention relates to an improved integrated process of *Jatropha* methyl ester preparation from whole seed capsules. More specifically, the invention relates to a method of dispensing with the need for excess methanol recovery through distillation, cost-effective resin treatment for the refining of methyl ester and utilization of co-streams for preparation of high density energy briquettes and Polyhydroxyalkanoate biodegradable polymer in efficient and cost-effective manner.

BACKGROUND OF THE INVENTION

Reference may be made to Australian Patent No. AU-A-15448/83 on *Jatropha curcas* oil for use with gasoline and diesel engines (assigned to Yuko Chemical Co. Ltd.). While this pioneering effort brought out the goodness of *Jatropha* oil, it is well known to those skilled in the art that raw oil is far too viscous to use in substantial proportions in modern day diesel engines.

Reference may be made to U.S. Pat. No. 6,399,800 by Haas et al. and US Patent Application No. 2004/0102640 A1 by Brunner et al. which disclose related methods of producing fatty acid alkyl esters through a combination of esterification and transesterification processes catalysed by acid and alkali, respectively. No mention is made of any of the inventions which are the subject matter of the present application.

Reference may also be made to German Patent Application No. DE 102,43,700 A1 wherein, methyl ester is obtained from a range of triglycerides including animal fat, using sulphuric acid and para-toluene sulphonic acid catalysts. No mention is made of the subject matter of the present application.

Reference may be made to the patent applications by Ghosh et al. (U.S. patent application Ser. No. 11/00239; PCT/IN04/00329 and accompanying national phase filings) wherein, an integrated process of production of *Jatropha* methyl ester from whole seed is disclosed integrated with recovery of by-products. The raw oil expelled from whole seed is neutralized with NaOH to reduce free fatty acid content and then transesterified with methanolic KOH with 5.0-5.5 mole of methanol per mole of triglyceride oil against the theoretical requirement of three moles of methanol per mole of triglyceride. The methyl ester is thereafter purified through washes with pure glycerol (4-5 kg per 100 kg of methyl ester) and thereafter washed with water to obtain product of >98% purity and satisfying all requirements as per EN14214 and ASTM specifications. The crude glycerol layer is subjected to distillation to recover methanol, then acidified to recover $K_2SO_4$ and soap-like matter, and thereafter subjected to distillation once again to recover glycerol in pure form, leaving behind a small amount of still bottom as waste. One drawback of the process is that not all of the oil is recovered in the form of methyl ester, a small portion being converted into soap which is formed in proportion to the free fatty acid content and, therefore, it is imperative that the free fatty acid content of the oil be maintained as low as possible. No mention is made of utilization of whole seed capsules as feedstock nor of any water less process of refining methyl ester nor of any process for production of polyhydroxyalkanoate from the crude glycerol.

Reference may be made to the article entitled "*On Road Testing of Advanced Common Rail Diesel Vehicles with Biodiesel from the Jatropha curcas Plant*" by S. Mandpe, S. Kadlaskar, W. Degen and S. Keppeler (2005-26-356, Proceedings of SAEINDIA Conference 2005) which narrates the performance of C-class Mercedes cars driven with the neat methyl ester prepared as per the process disclosed by Ghosh et al. in the reference cited above.

Reference may be made to the European project entitled "*Local and Innovative Biodiesel*" (Altener Contract No. 4.1030/C/02-022; http//www.fedarene.org/publications/projects/contract/biodiesel/home.htm; Coordinator—EREN; Report courtesy Austrian Biofuels Institute E.V.—Co-contractor), wherein, an evaluation was made of methyl esters from around the world prepared by different agencies using the same or different feedstocks. The *Jatropha* methyl ester (JME-05-728) prepared as per the process of the invention of Ghosh et al. (PCT/IN04/00329; U.S. patent application Ser. No. 11/00239) gave the best engine performance in terms of power derived, fuel consumption and long term performance.

Reference may be made to the article entitled "*Biofuel—The little shrub that could—may be*" by D. Fairless (*Nature*, 449, 2007, pp. 652-655) which narrates the promise that *Jatropha curcas* holds as a suitable source of biodiesel.

Reference may be made to the report of LEA Bioenergy Task 40 (http://www.city.northbay.on.ca/business/presentations/woodPellets/Global %20wood%20pellets% 20market% 20and%20industry%20Nov%2007%20report.pdf) which discusses at length the prospects of biomass pellets as fuel source and the desired specifications.

Reference may also be made to the article entitled "*Prospects for Jatropha Methyl Ester (Biodiesel) in India*" by Ghosh et al. (*Int. J. Environ. Stud.* (Taylor & Francis, U.K.)—special issue on India's future energy options; 2007, 64, pp 659-674) which states the possibility of making briquettes from whole seed capsules of *Jatropha curcas* after separation of seeds. There is, however, no mention of any process through which such briquettes are made nor of their specifications.

Reference may be made to the article entitled "*Comparison of purification methods for biodiesel*" by M. Berrios and R. L. Skelton (*Chemical Engineering Journal*, 2008, pp. 459-465) wherein different methods of purification of biodiesel are described. Specifically, a comparative assessment has been made of water washing, use of ion exchange resin, and use of magnesium silicate as adsorbent.

Reference may be made to German patent No. DE 43 01 686 C1 by Gross et al. which discloses a process of production of methyl ester of rape seed oil by a distillation process which makes it a water-less process.

Reference may be made to the article entitled "Refining of biodiesel by ceramic membrane separation" by Wang et al. (*Fuel Processing Technology*, Article in Press, 20 Dec. 2008) wherein ceramic membranes of the pore sizes of 0.6, 0.2 and 0.1 μm were used in an attempt to remove the residual soap and free glycerol through a water-less process.

Reference may be made to the web site of Purolite (http://www.desmoparts.com/filters/purolite/HBD-Purolite%20Regeneration.pdf) which mentions about resin PD206 [Purolite Application note/Purolite PD-206 Guide] which can be used in two ways: one for removing moisture, methanol and glycerol and the other for ion exchange of catalyst, salts and soaps exchanging primarily sodium ($Na^+$) of the catalyst for hydrogen ($H^+$) on the resin. It is reported that after adsorption of water, methanol, and glycerol from biodiesel the volume of resin expands to twice the dry volume of resin. Moreover, there is an estimated 10% attrition due to bead breakage in the first regeneration. Bead breakage and loss of functional groups are the limiting factors determining the number of times PD206 can be regenerated and there is presently a need to replace PD206 after 2-4 regenerations. Suffice it to say that use of resin would be viable only if the load of impurities in the methyl ester is at the barest minimum.

Reference may be made to U.S. Pat. No. 5,424,467 by Barn et al. wherein, the purification of methyl ester and utilization of crude glycerol layer are disclosed. It is stated therein that mono- and diglyceride impurities in the glycerol layer can be converted into the desired methyl ester through reaction with additional amounts of methanol. Methanol in the glycerol layer is recovered by distillation. No mention is made of recovery of methanol through the process of further reaction with triglyceride oil which is disclosed in the present invention.

Reference is once again made to the patent applications by Ghosh et al. (U.S. patent application Ser. No. 11/00239; PCT/IN04/00329) wherein an efficient method is provided that uses very small amounts of pure glycerol (ca. 3 kg per 100 kg of methyl ester) to wash the crude methyl ester which process minimizes residual impurities in the methyl ester while enriching them in the crude glycerol layer. As a result methanol recovery from methyl ester is not necessary while such recovery from glycerol layer is undertaken by distillation. The reported recovery of methanol is ca. 70-80% of the excess methanol used. No mention is made of any other possible methods of recovering methanol from the glycerol layer, nor any mention of making polyhydroxyalkanoates (PHAs) from the co-product streams.

Patent application No. WO/2006/084048 relates generally to bio-diesel fuels, and more particularly to a process for converting the waste glycerol generated by traditional transesterification processes into a miscible and combustible component of a bio-diesel fuel.

Reference may be made to the article entitled "From glycerol to value-added products" by M. Pagliaro et al. (Angew. Chem. Int. Ed. (2007), 46, 4434-4440) wherein, various products derived from glycerol, e.g. propylene glycol, 1,2-propanediol, soaps, drugs, explosives, detergents, cosmetics, dihydroxy-acetone (DHA), acrolein, epichlorohydrin, syngas-fuels, glycerol carbonate, anti-freezing agent, catalytic conversion to polymers, etc., are described. However, there is no reference to production of biopolymer (PHAs). Reference may be made to U.S. Pat. No. 7,388,034 by Goetsch et al. which discloses a method of producing methanol from the crude glycerol by-product of biodiesel process.

Reference may be made to "Biopolymers for Medical and Pharmaceutical Applications", Vol. 1&2, A. Steinbüchel and R. H. Marchessault, Wiley-VCH Verlag GmbH & Co. KGaA (2005) and reference therein which cite numerous prior art pertaining to the preparation and properties of PHA. No reference is made to the approach to PHA production pertaining to the present invention.

Reference may be made to the paper by G. N. M. Huijberts et al. entitled "*Pseudomonas putida* KT2442 cultivated on glucose accumulates poly(3-hydroxyalkanoates) consisting of saturated and unsaturated monomers" (Applied and Environmental Microbiology, February 1992, Vol 58, Issue 2, pp 536-544) wherein growth of recombinant strain of *Pseudomonas putida* KT2442 was studied using different carbohydrates like glucose (2%), fructose (2%) and glycerol (4%) in E2 medium, producing PHA having similar monomer composition. The yield of PHA was 20.5% (w/w) with respect to cell dry weight.

Reference may be made to the paper by Taniguchi et al. entitled "Microbial production of poly(hydroxyalkanoate)s from waste edible oils" (Green Chem. 2003, 5, pp 545-548). The paper describes the results obtained with *Ralstonia eutropha* in a 2-stage fermentation process (one for growth of culture and the other for production of polyhydroxyalkanoate) which gave a maximum PHA yield of 83% with respect to cell dry weight when palm and lard were used. The production medium also contained inorganic nutrients/micronutrients while the growth medium contained nutrient broth which is costly.

Reference may be made to the research paper by R. D. Ashby et al. entitled "Bacterial poly(hydroxyalkanoate) polymer production from the biodiesel co-product stream." (Journal of Polymers and the Environment, 2004, volume 12, pp 105-112) wherein, *Pseudomonas oleovorans* and *Pseudomonas corrugata* were used for PHA production from co-product stream of soya based biodiesel production (CSBP) stream containing glycerol, fatty acid soaps and residual fatty acid methyl esters at 1% to 5% concentration in a 2-stage fermentation process. The alkaline co-product stream (pH 13) was neutralized with 1 N HCl to pH 7 before using as substrate. The bacteria were initially grown in Luria-Bertani (LB) broth, which comprises several costly constituents including peptone and thereafter, the cells were transferred into the production medium containing the neutralized co-product stream and additional nutrients/micronutrients. The polymer cell productivity was only 42% of cell dry weight (CDW) with *Pseudomonas corrugata* while polymer yield with respect to glycerol was <5% even under optimized conditions. Such conditions include use of special media enriched in costly nutrients.

Reference may be made to the research paper by E. J. Bormann and M. Roth. entitled "The production of polyhydroxybutyrate by *Methylobacterium rhodesianum* and *Ralstonia eutropha* in media containing glycerol and casein hydrolysates" (Biotechnology Letters, 1999, Volume 21, pp 1059-1063) wherein the production of polyhydroxybutyrate (PHB) by these bacteria was in medium containing glycerol combined with casein peptone or casamino acids. The glycerol was used at a concentration of 2.5%, 5% and 7.5%. The yield of polymer was reported to be 17% (w/w) with respect to glycerol while, the polymer content as a percentage of cell dry weight was 39±6%.

Reference may be made to the research paper by Koller M., et al. entitled "Production of polyhydroxyalkanoates from agricultural waste and surplus materials" (Biomacromolecules, 2005, Volume 6, pp 561-565) wherein polyhydroxyalkanoate was obtained from whey hydrolysate (0.55%) and glycerol liquid phase (1.6%) supplemented with meat and bone meal by an osmophilic organism. The yield of PHA with respect to glycerol was 23% and the polymer had molecular weight of 253 kDa and melting endotherms at 128° C. and 139° C.

Reference may be made to the paper by Ito et al. (J. Bioscience & Bioengineering, 2005, 100, pp 260-265) which describes the biochemical production of hydrogen and ethanol from the glycerol-containing wastes discharged after biodiesel manufacturing process. It is reported that the biochemical activity is much lower than with pure glycerol due to the presence of high salt content in the wastes.

It will be evident from the prior art that no cost-effective process has been disclosed for production of PHA from biodiesel co-product streams and even with the use of costly co-nutrients and cumbersome 2-step process, the PHA yield with respect to cell dry weight is generally reported to be <50%. The prior art also teaches us that attempt to use glycerol-containing wastes led to much lower biochemical productivity than pure glycerol which is ascribed to the presence of high levels of salt. The present invention seeks to overcome all of these basic limitations and to evolve a novel, simplified and cost-effective process of producing PHA from glycerol co-product stream of methyl ester process starting from *Jatropha* whole seed capsule. Several other associated improvements in the process such as (i) best utilization of problematic waste, particularly oil sludge generated during mechanical expelling of oil and still bottom of glycerol distillation process, (ii) alternative solution to distillation of methanol from crude glycerol layer, and (iii) cost-effective resin treatment of glycerol-washed methyl ester also form part of the present invention.

OBJECTS OF THE INVENTION

The main object of the present invention is to provide an improved and integrated process for the preparation of fatty acid methyl ester (biodiesel) from whole seeds of *Jatropha curcas*.

Another object of the present invention is to produce biodiesel with least energy input and zero effluent discharge.

Another object is to show that 90% of the 0.58 mole equivalent excess methanol and almost all of the KOH catalyst used in the process of transesterification are confined to the glycerol layer through the process of glycerol washing disclosed in the prior art.

Another object is to show that, since potassium and sodium ions are present only in trace amounts in the methyl ester layer after glycerol washing, it may be practical to remove the residual amounts of these cations through treatment with ion exchange resin and thereby bring down their concentrations to the demanding levels specified.

Another object is to dispense with the need for distillation of methanol for its recovery.

Another object is to mop up 70-90% of the methanol in glycerol layer through sequential reactions with additional amounts of triglyceride oil.

Another object is to utilize the crude glycerol after mopping up of methanol as a carbon and nutrient source in growth and production media for microbial synthesis of biodegradable polyhydroxyalkanoate polymer in cost-effective manner.

Another object is to utilize the cake obtained after expelling oil from *Jatropha* seeds as a source of amino acids and other nutrients in the growth medium and thereby to dispense with costly media such as King's B medium and Zobell's marine medium.

Another object is to show that toxic impurities such as phorbol esters and curcin which are indicated to be present in the oil cake do not hamper PHA production in the processes of the present invention.

Another object is to demonstrate efficient production of PHA polymer having physico-chemical properties similar to those of standard PHA.

Another object is to show that a marine bacterial isolate (99.63% sequence similarity with *Halomonas hydrothermalis*) from the Arabian Sea gives a yield of 75% PHA with respect to cell dry weight by inoculating the culture directly into a medium containing the alkaline crude glycerol layer and the hydrolysate derived from deoiled *Jatropha* cake and without use of any other nutrient/micronutrients and without any other intervention such as sparging, pH adjustment, temperature control, etc.

Another object is to achieve such PHA production in the simplest and cheapest manner and in the shortest possible time

IN THE DRAWING(S) ACCOMPANYING THIS SPECIFICATION

SUMMARY OF THE INVENTION

Figure 1:
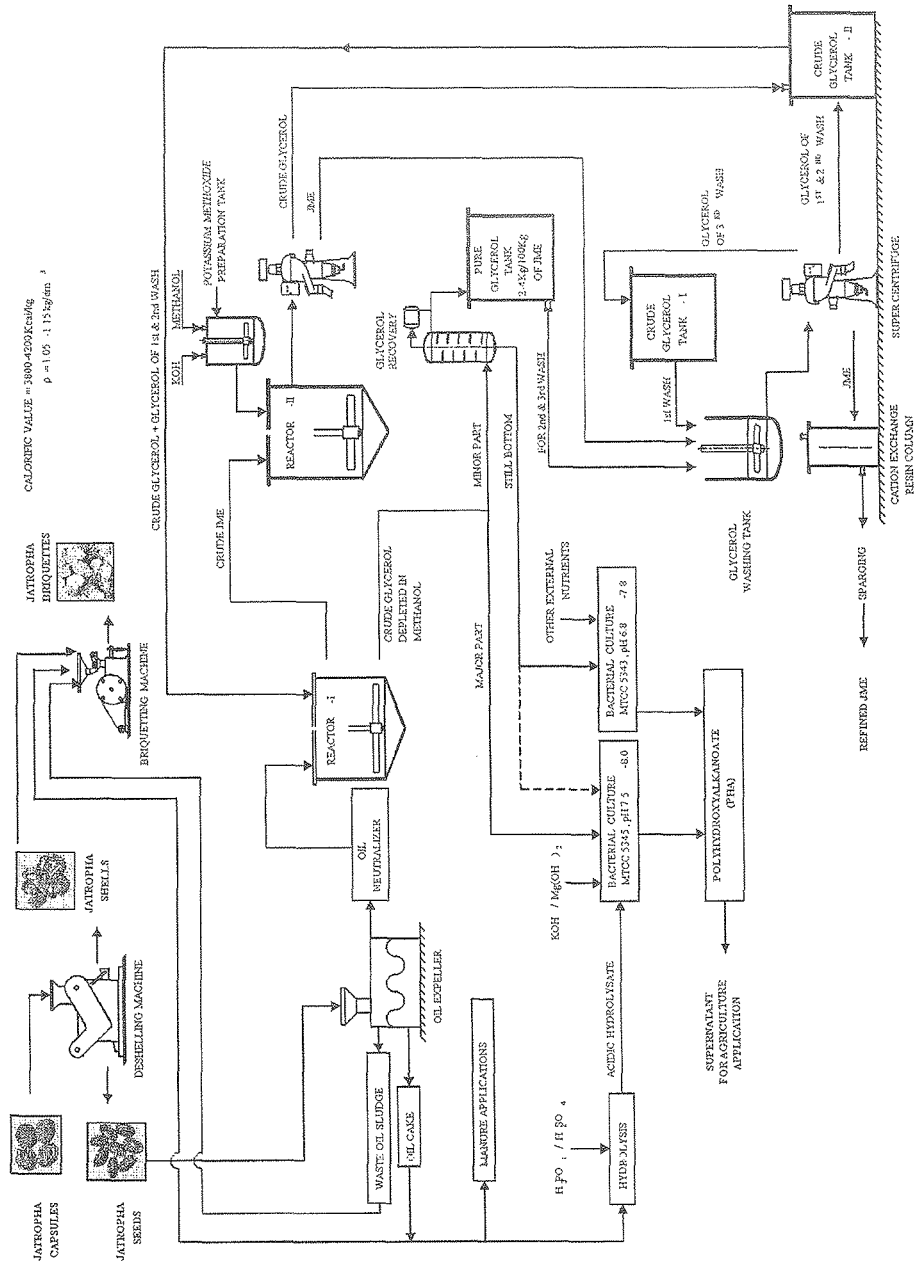
FIG. 1 represents the schematic view of preparation of Methyl Ester and allied products from whole seed capsules of *Jatropha curcas* for the present Invention.

Accordingly the present invention provides an integrated process for the preparation of *Jatropha* Methyl Ester (JME) and by-products from the encapsulated seeds of *Jatropha* containing 1.06% of free fatty acids (FFA) and the said process comprising the steps of:
(i) mechanically deshelling capsulated seeds of *Jatropha* in deshelling machine to obtain *Jatropha* shells and *Jatropha* seeds;
(ii) expelling *Jatropha* oil, *Jatropha* oil cake having 4-6% nitrogen and waste oil sludge from the *Jatropha* seeds obtained in step (i), using oil expeller;
(iii) neutralizing *Jatropha* oil obtained in step (ii) with base;
(iv) transesterifying one part of neutralized *Jatropha* oil obtained in step (iii) with alcohol and base with stirring for 10 to 20 minutes and separating crude glycerol layer GL1 and crude *Jatropha* methyl ester (JME);
(v) washing crude JME obtained in step (iv) three times with pure glycerol layer to separate three impure glycerol layers GL2,GL3 and GL4 containing methanol and KOH to obtain Glycerol washed JME-$G_3$W;
(vi) purifying JME-$G_3$W obtained in step (v) to remove alkali metal impurities;
(vii) treating part of remaining neutralized oil obtained in step (iii) with glycerol layers GL5 (GL1+GL2+GL3) obtained in step (iv) and (v) to obtain JME and glycerol layer GL6;

(viii) separating JME and glycerol layer GL6 obtained in step (vii);

(ix) treating glycerol layer GL6 obtained in step (viii) with remaining part of neutralized oil for mopping up of methanol to obtain JME and glycerol layer GL7;

(x) separating JME and glycerol layer GL7 obtained in step (ix);

(xi) using glycerol layer GL7 as obtained in step x) directly for the production of polyhydroxyalkanoates (PHAs) or for the neutralization of alkali with sulfuric acid to obtain pure glycerol and still bottom GL8;

(xii) combining JME-$G_3W$ obtained in step (vi) and JME obtained in step (viii) and (x) to obtain combine methyl ester; and (xiii) transesterifying combined methyl ester obtained in step (xii) with methanolic KOH to yield pure *Jatropha* methyl ester (Biodiesel) having total glycerol of 0.088% and free glycerol of 0.005%.

In one embodiment of the present invention, the present invention provides an integrated process for the preparation of byproducts and the said process comprising the steps of a. briquetting the *Jatropha* shells obtained in step (i) in briquetting machine with the addition of waste oil sludge obtained in step (ii) to obtain *Jatropha* briquettes of 1.05-1.10 g/cm$^3$ density as by product;

b. hydrolyzing *Jatropha* oil cake having 4-6% Nitrogen obtained in step (ii) with $H_3PO_4$, $H_2SO_4$ to obtain *Jatropha* oil cake hydrolysate (JOCH) as byproduct.

In another embodiment of the present invention, the present invention provides an integrated process for the preparation of byproducts polyhydroxyalkanoates (PHAs) and the said process comprising the steps of I. inoculating 1-10% of soil bacteria MTCC 5443 or marine bacteria MTCC 5445 more preferably marine bacteria MTCC 5445 seed culture in to growth-cum production medium containing 2-10% (w/v) still bottom GL8 or GL7 or combination thereof and incubating for the period of 24-96 hrs at a pH of 7.0-8.0 at a temperature in the range of 25-40° C. to allow fermentation;

II. harvesting the cell by centrifugation of the ferment to obtain pellets;

III. recovering solid polymer by centrifugation of the pellets;

IV. washing the solid polymer with water and methanol to obtain PHA;

V. dissolving 0.5 to 5% of PHA in chloroform to obtain PHA film.

In yet another embodiment of the present invention, sun dried whole seed capsules enhance the keeping characteristics and the oil has a free fatty acid content of only 0.5-2.0% when the seeds are encapsulated thereby increasing the yield of methyl ester.

In yet another embodiment of the present invention, wherein deshelling was done in a specially designed deshelling machine comprising of (i) a capsule breaker consisting of rotating drum that breaks open shells by attrition with stationary surface without damaging the seeds, (ii) sloping vibrating sieves for separating seeds from the shells and directing seeds to move in opposite direction to shells, and (iii) using the blower to blow off the shells which are collected separately with no loss of seed in the shells.

In yet another embodiment of the present invention, base is selected from the group consisting of potassium hydroxide or sodium hydroxide more preferably potassium hydroxide.

In yet another embodiment of the present invention, alcohol is selected from the group consisting of methanol or ethanol more preferably methanol.

In yet another embodiment of the present invention, JME-$G_3W$ layer is purified by using macroporous cation exchange resin to remove alkali metal impurities.

In yet another embodiment of the present invention, macroporous cation exchange resin is prepared by using styrene-divinylbenzene copolymers and sulfuric acid.

In yet another embodiment of the present invention, styrene-divinylbenzene copolymer is prepared by suspension polymerization of styrene using cetyl alcohol as porosogenic agent.

In still another embodiment of the present invention, JME-$G_3W$ layer subjected to resin treatment had a maximum [$Na^+$] and [$K^+$] impurity level of 15-30 ppm to <0.5 ppm, methanol impurity level of 0.4-0.6% (w/w), moisture level of 500-1500 ppm, total glycerol content of 0.2-0.3% (w/w) and lower free fatty acid content of 0.15-0.25% (w/w).

In still another embodiment of the present invention, still bottom is defined as the residue left after a successful cycle, consisting mainly of solids and free liquids that have no value in terms of further distillable solvent/product.

In still another embodiment of the present invention, the briquetting was done in a briquetting machine comprising (i) an inclined screw feeder, (ii) a mixing device equipped with agitator and with opening to feed additives, (iii) a compression system consisting of a die to mold the briquette and hydraulic system to generate high pressure for compaction, and (iv) briquette conveying system for cooling the briquette formed.

In still another embodiment of the present invention, the shells obtained had a bulk density of 0.08 g/cm$^3$ and calorific value of 3700 kcal/kg.

In still another embodiment of the present invention, growth medium is selected from the group consisting of King's B medium, Zobell's marine medium and deoiled *Jatropha* oil cake hydrolysate (JOCH) with GL7 and GL8.

In yet another embodiment of the present invention, the PHA yields with respect to cell dry weight were in the range of 69% to 77%.

In yet another embodiment of the present invention, the PHA obtained matched the NMR profile of standard PHA, the melting point by DSC was 166.2° C. and GPC data gave $M_w$, $M_n$ and $M_w/M_n$ (polydispersity index) values of 35990, 24583 and 1.46, respectively.

In yet another embodiment of the present invention, the above steps may equally apply to a variety of triglyceride oils.

DETAILED DESCRIPTION OF THE INVENTION

The aim of the present invention is to bring about all-round improvement in the process of production of *Jatropha* methyl ester with maximum attention to decentralized production employing simple unit operations. Traditionally, the farmers de-shell the dried whole fruit but this leads to no utilization of the shells, and consequently, the price of seeds is higher because only the seeds have to bear the brunt of the cost besides the labour cost entailed in de-shelling the fruits. In the course of the invention it has also been found advantageous to leave the seed encapsulated as the shell offers a second layer of protection which preserves the characteristics of the oil seed besides keeping them clean. This is especially important when methyl ester is obtained through base catalysis, since excess free fatty acid has to be eliminated through neutralization leading to decrease in the yield of methyl ester. It is imperative therefore, to devise machines which can mechanically de-shell the sun dried capsules in a manner that the seeds are obtained intact and cleanly separated from the shells, and such seeds are used up soon after. Further, since the shells are now collected at a single point, there is strong motivation to ensure that these shells, having bulk density of only 0.08 g/cm$^3$ and calorific value of 3700 kcal/kg, can be briquetted so that they are easy to transport and the rural folk can use them directly rather than firewood or more costly alternatives. There is once again a motivation to ensure that suitable processes are devised which allow the desired level of compaction of the empty shells into sturdy briquettes providing high energy density. Both these operations are successfully disclosed in the present invention, making good use of small amounts of waste oil generated during the mechanical expelling of oil from seeds and also making use of a small part of the deoiled cake to produce briquettes having density of 1.05-1.15 g/cm$^3$ and calorific value of ca. 4000 kcal/kg as per desired specifications.

Although the best of the prior art discloses very efficient processes of transesterification and post-transesterification of *Jatropha* methyl ester, and the methanol usage is also comparatively low (only 0.55-0.75 mole equivalent excess), nevertheless it is important that this methanol be recovered to the maximum extent possible. The glycerol washing process to purify the methyl ester disclosed in the prior art leaves very little of the methanol in the methyl ester; instead, it is confined to the extent of 90-95% in the glycerol layer. Since the methyl ester after glycerol wash also has extremely low levels of residual alkali catalyst as confirmed through ion chromatographic measurements in the course of the invention, the question also arises as to whether a water wash of the methyl ester is at all necessary. Instead, a dry process based on use of ion exchange resin is disclosed. What makes the present process inventive is the fact that the load on the resin is extremely low and, therefore, substantial amounts of the methyl ester can be treated with small bed volumes of resin without regeneration.

With regards to the crude glycerol layer, the question arises as to what is the highest level of simplification possible in its effective use. As disclosed in the present invention, if the excess methanol in the glycerol layer can be removed by simple means, then the rest of the mass can be utilized directly for preparation of polyhydroxyalkanoates in simple and cost effective manner. The question subsequently arose in our mind as to whether distillation of methanol from the glycerol layer—which entails considerable losses unless provided with chilling unit—is the only option. As disclosed in the present invention, reverse uptake of methanol into fresh lot of *Jatropha* oil is feasible to the extent that 80-95% of the methanol can be gainfully utilized in this manner. This is because the glycerol layer also contains partly active alkali catalyst (KOH) and therefore has all the ingredients to promote some extent of methyl ester formation once fresh oil is added and adequate agitation provided. However, the methanol and catalyst amounts are not adequate to realize a perfect methyl ester and this step is followed up by a second operation which enables such pure ester with <0.15% (w/w) total glycerol to be produced. The net outcome is the realization of glycerol layer depleted in methanol and cut back in methanol usage in the second step such that, the overall requirement of excess methanol in unrecoverable form is <0.15 mole equivalent without any distillation step and without in any manner compromising on methyl ester quality.

Once the methanol is mopped up, the glycerol layer is demonstrated to be an excellent source of nutrient for efficient and cost-effective production of polyhydroxyalkanoate by a marine bacterial culture isolated in the course of the invention. The hydrolysate produced from *Jatropha* deoiled cake obtained through reactive extraction with hot phosphoric acid/sulphuric acid is shown to be an ideal complementary partner to the crude glycerol, the two in tandem providing the nutrients required for PHA production by the marine bacterial culture without any deliberate temperature control. The two together also help to neutralize (acid-base) each other to some extent thereby driving down the cost of neutralization. There are several additional inventions such as merging the normal 2-stage process into a single step, dispensing altogether with all nutrients/micronutrients by deriving the essential phosphate buffers and essential elements from the hydrolysate and glycerol layer besides carbon and nitrogen. In a decentralized operation, where such a plant will be set up in the vicinity of agricultural fields, the supernatant after recovery of harvestable biomass can be discharged directly into the field for soil fertigation or can even be used as a foliar spray.

Although a large fraction of the glycerol layer can be utilized in this manner, a small fraction of the glycerol layer is required to recover pure glycerol (2-4 kg glycerol per 100 kg of methyl ester) essential for the critical glycerol washing step. It is further demonstrated that the still bottom remaining after glycerol recovery is an equally effective nutrient and promoter for PHA production by a soil bacterial culture, the efficiency of production being nearly twofold higher than with pure glycerol. Thus, the problematic waste is found to be an ideal source of nutrients. The PHA obtained by this process has low polydispersity index of 1.46 while exhibiting an NMR pattern similar to that of standard PHA.

The still bottom can also be used in combination with the remaining crude glycerol avoiding thereby the need for two separate operations and making use of MTCC 5445 in this composition.

All of these inventions taken together lead to an improved integrated process of production of methyl ester from sun dried whole seed capsules of *Jatropha curcas* with gainful utilization of co-product streams. The integrated scheme of the present invention is shown in FIG. 1.

Inventive Features:

(i) Establishing that whole seed capsule helps maintain oil quality better than the de-shelled seeds in terms of the free fatty acid content.

(ii) Utilising the small amount of waste oil in the form of sludge—which is inevitably generated during the process of mechanical expelling and causes problems of disposal—to produce denser and stronger briquettes from the empty shells while also adding to the calorific value of the briquettes.

(iii) Recognising further that a part of the de-oiled cake can be used to make better briquettes than obtained with the shells alone.

(iv) Reacting the glycerol layer containing partly active catalyst and the excess methanol taken for transesterification with additional amount of refined *Jatropha* oil in two stages to mop up 70-90% of this methanol. The oil/methyl ester mixture is then further reacted with alkali and methanol so that unreacted and partially reacted oils are completely converted into methyl ester, and this cycle of mopping up methanol from glycerol layer followed by transesterification to a perfect product is repeated continuously to dispense with methanol distillation from crude glycerol layer.

(v) Ascertaining that the glycerol washing process removes almost all of the spent catalyst from the methyl ester layer and thereafter recognizing that it may be an attractive proposition to subject the glycerol-washed methyl ester layer to cation exchange resin treatment to achieve the desired sub-ppm levels of sodium and potassium impurities without need for water wash while ensuring that large amounts of methyl ester can be treated with minimum bed volume of resin.

(vi) Dividing the crude glycerol layer depleted in methanol into a 1:3 volume ratio and recovering distilled glycerol from the smaller fraction after work up—so that it can be reused in the subsequent batch for glycerol washing as described in the prior art.

(vii) Isolating bacteria MTCC 5443 from soil which enables PHA to be produced from the still bottom of 1 in a manner that is more advantageous than with pure glycerol as carbon source and thereby converting a problematic waste into a useful raw material for PHA production.

(viii) Identifying through the process of screening of marine bacteria a potent isolate (MTCC 5445) which efficiently utilises the larger volume of crude glycerol layer directly, together with the hydrolysate of *Jatropha* deoiled cake, as the only nutrients in a fermentation process leading to production of PHA with yield of 75-80% with respect to cell dry weight. Further, combining the steps of growth and production undertaken separately in the conventional processes of PHA production into a single operation and thereby simplifying the process. Still further, adding the still bottom from 1 into the larger fraction of glycerol layer and subjecting the resultant mass to fermentation with MTCC 5445. Also dispensing with the need for temperature control after demonstrating tolerance of the process to temperature variations over 28~38° C.

(ix) Recognising that in preparing the hydrolysate of deoiled cake used in the fermentation process, it is advantageous to use phosphoric acid and thereafter to neutralize the acid extract with the alkaline glycerol layer itself—and additional KOH/Mg(OH), as may be required—so that the resultant salts support the PHA production instead of thwarting it.

The following examples are given by way of illustration and should not be construed so as to limit the scope of the invention.

EXAMPLE 1

A jute bag containing 50 kg of sun-dried *Jatropha* seed capsules which was 3 months' old was cut open and it was found that while most of the capsules were intact, some capsules had broken and the seeds had come out. 50-100 g of such seeds collected randomly was crushed into a powder and 25 g was taken for Soxhlet extraction using n-hexane. Seeds were also removed from the intact capsules sampled randomly and subjected to similar extraction. It was found that exposed seeds had free fatty acid (FFA) content of 3.68% (w/w) whereas the encapsulated seeds showed FFA content of 1.06%. Another bag was opened and sampling carried out as above. The exposed and encapsulated seeds gave FFA values of 2.46% and 1.09%, respectively, i.e., the two observations were similar suggesting that whole seed capsules preserve oil better. Since, higher FFA reduces methyl ester yield as per the prior art of transesterification with alkali catalyst, this example teaches us that it is better to leave seeds in encapsulated form and de-shell the seeds just prior to making of methyl ester.

EXAMPLE 2

The whole seed capsules of Example 1 above were mechanically de-shelled in a specially designed machine. The 1 Tonne per hour (TPH capsule) machine comprised of (a) a capsule breaker consisting of rotating drum that breaks open shells by attrition with stationary surface without damaging the seeds, (b) sloping vibrating sieves that separate seeds from the shells and direct seeds to move in opposite direction to shells, and (iii) blower that blows off the shells which are collected separately with no loss of seed in the shells. Oil was expelled mechanically from the whole seeds whereas the shells were subjected to briquetting in a specially designed machine. Briquettes were made in a 0.5 TPH briquetting machine comprising (a) an inclined screw feeder, (b) a mixing device equipped with agitator and with opening to feed additives, (c) a compression system consisting of a die to mold the briquette and hydraulic system to generate high pressure for compaction, and (d) briquette conveying system that also cools the briquette formed. It was found that the briquettes were fragile but upon adding waste oil sludge generated in the process of mechanical expelling of oil into the shells, the briquettes became sturdier and had density of 1.07-1.15 g/cm$^3$ and calorific value higher than 3700 kcal/kg recorded for the empty shells without such addition of oil. The briquettes obtained had dimensions of 6 cm diameter and 14 cm length.

EXAMPLE 3

*Jatropha* oil expelled as in Example 2 above was neutralized with aqueous NaOH to lower the free fatty acid (FFA) content to 0.12% (w/w). 64.5 g MeOH (1.58 mole equivalent) and 8.33 g KOH were taken together and added into 370 g of neutralized *Jatropha* oil in a round bottom flask and the contents stirred for 15 min at room temperature with overhead stirrer to effect transesterification. The crude glycerol layer weighing 63.87 g was separated and the methyl ester layer was then washed three times with 5.53 g, 5.76 g and 5.56 g of pure glycerol successively and these washings generated 11.69 g, 7.10 g and 6.29 g of glycerol (with methanol and KOH as impurities), respectively. In step 2, the crude glycerol and the first two washings were combined and the combined layer containing 16.01 g methanol was again reacted with 300 g of neutralized *Jatropha* oil under continuous agitation at 100-300 rpm (paddle type pitch blade agitator) for 2 h. The two layers were again separated and the glycerol layer was treated yet again with 70 g of additional neutralized oil under vigorous overhead stirring for 2 h. The spent glycerol layer contained 3.15 g of methanol, i.e., 80.3% of methanol in the glycerol layer could be mopped up through this process. The crude methyl ester layers obtained in step 2 were treated with additional amounts of methanolic KOH (63.6 g MeOH and 8.2 g KOH) and thereafter washed with glycerol as in step 1 followed by water wash. The combined methyl ester yield from both steps was 710 g (95.9% yield with respect to total neutralized oil taken) while the total glycerol and free glycerol values were 0.10% (w/w) and 0.01% (w/w), respectively. The glycerol layers obtained in step 2 could be treated with neutralized oil in similar fashion to mop up methanol. This example teaches us how to mop up methanol from crude glycerol layer and thereby to dispense with distillation of methanol.

EXAMPLE 4

The experiment of example 3 was scaled up thousand fold in the pilot plant. 740 kg of neutralized oil was taken. Half of the oil was transesterified in single step through reaction with methanolic KOH solution [KOH (78.8% purity) 8.33 kg; methanol 64.5 kg (1.58 mole equivalent)] under stirring at room temperature for 15 min in Reactor II of FIG. 1. The glycerol layer (GL 1) was separated and weighed 79.55 kg. The methyl ester layer (crude JME) was then treated three times with 5.55 kg each of glycerol and the glycerol layers were separated each time, the final separation being done using a super centrifuge. The separated glycerol wash layers weighed 11.28 kg (GL2), 8.06 kg (GL3) and 6.11 kg (GL4), respectively. Methanol, KOH and overall K balance up to this stage is shown in Table 1 below. It can be seen from the data that 89.3% of the excess methanol taken ends up in the glycerol layers (GL1-GL4) and that there is, therefore, good opportunity to recover this excess methanol from the glycerol layers—without recourse to distillation—by the method of the present invention. A part of the glycerol-washed methyl ester layer (designated as JME-G$_3$W) was thereafter treated with ion exchange resin to eliminate residual alkali as described below while the remaining part was processed as per the Prior art to give pure methyl ester having total glycerol of 0.12% and free glycerol of 0.01%.

TABLE 1

MeOH and K balance for transesterification-cum-glycerol wash of first lot of 370 kg of refined Jatropha oil of Example 1

| Sample no. | Identity | Methanol/ kg | K (by flame photometer)/ kg | Extrapolated theoretical KOH based on K/kg | Actual KOH by titration/ kg |
|---|---|---|---|---|---|
| 1 | GL 1 | 19.07 | 5.43 | 7.79 | 3.67 |
| 2 | GL 2 | 0.83 | 0.10 | 0.15 | 0.11 |
| 3 | GL 3 | 0.45 | 0.02 | 0.03 | 0.02 |
| 4 | GL 4 | 0.24 | — | — | 0.01 |
| 5 | JME-G$_3$W | 2.54 | 0.006 (by IC of water wash) | | |
| 6 | Total | 23.13 | | | |
| 7 | Expected (based on 0.58 mole equivalent excess) | 23.68 | | | |

Added Methanol = 64.50 kg and added KOH = 8.33 kg (78% alkalinity by titration)
Methanol expected to be consumed in biodiesel formation = 40.82 kg So 23.68 kg should remain. Estimated by experiment: 23.13 kg The glycerol layers GL1, GL2 and GL3 above were combined (designated as GL5) and the total weight was 98.89 kg. This was then taken together with additional 300 kg of neutralized *Jatropha* oil of Example 3 and the contents were subjected to vigorous stirring at room temperature for 2 hours in Reactor I of FIG. 1. The two layers were allowed to separate and the crude methyl ester was decanted into Reactor II for further transesterification. The glycerol layer (GL6) in the reactor was once again reacted with the remaining 70 kg of refined *Jatropha* oil from Example 3 and the two layers were allowed to separate and the methyl ester layer was decanted from the top and added into Reactor II already containing the first lot of crude methyl ester. As can be seen from the Table 2 below, analysis of the resultant glycerol layer (GL7) showed that 71.3% of the methanol in GL5 was mopped up by the treatment with the two lots of oil. The combined layers of crude methyl ester were thereafter treated once again with methanolic KOH [KOH (78.8% purity) 8.33 kg; methanol 64.5 kg (1.58 mole equivalent)] in Reactor II and subjected to glycerol wash followed by water wash to yield pure methyl ester having 0.088% total glycerol and 0.005% free glycerol. The crude glycerol along with washings can once again be treated with oil to mop up methanol as undertaken above. The example teaches us that the process of mopping up of methanol from crude glycerol is amenable to scale up. The data of Table 2 further teaches us that a fraction of the KOH in the glycerol layer is also mopped up.

TABLE 2

| Identity | Weight of glycerol layer (kg) | MeOH (kg) | K (by flame photometer)/ kg | Extrapolated theoretical KOH based on K/kg | Actual KOH by titration/ kg |
|---|---|---|---|---|---|
| GL5 | 98.89 | 20.35 | 5.55 | 7.97 | 3.80 |
| GL6 | 96 | 9.09 | 5.23 | 7.51 | 3.14 |
| GL7 | 90 | 5.83 | 4.74 | 6.81 | 2.36 |

It may be noted that although in the example above the crude methyl ester obtained after reaction with GL5 was once again treated with 1.58 mole equivalent of methanol, it is possible to subtract the methanol mopped up by the crude methyl ester layer to maintain an overall 1.58 mole ratio of methanol to neutralized oil as demonstrated in Example 6 below.

EXAMPLE 5

JOCH was prepared as follows: 100 g of *Jatropha* oil cake having 4-6% nitrogen, as obtained after expelling oil mechanically from whole seed as in Examples 3 and 4, was taken in a conical flask and 350 mL of acid solution containing a mixture of 8N H$_3$PO$_4$ and 2 N H$_2$SO$_4$ was added. The flask (without cap) was kept on hot plate at 100° C. for five hours. After that it was cooled to room temperature. The suspension was then neutralized with 330 ml of a solution containing 148 g KOH (neutralization may also be effected with alkaline GL7) into which was also added 19.1 g of solid Mg(OH)$_2$. This was done to yield salts which have buffering action and also contribute to the nutrient value of the hydrolysate. After that the contents were vacuum filtered on Buchner funnel (Whatman No. 40 filter paper). The pH was adjusted in the range of 5.5-8.5. The carbon content in the hydrolysate was 2.31% (w/v) and the bound nitrogen content was 0.48% (w/v). *Jatropha* oil cake having 4-6% (w/w) N, was treated with hot acidic aqueous solution of H$_3$PO$_4$/H$_2$SO$_4$.

EXAMPLE 6

The experiment of Example 4 was repeated except that after treatment of second lot of oil with GL4, the combined layers amounting to approximately 370 kg were reacted with 8.33 kg of KOH, as before, but with only 50.57 kg of methanol instead of 64.5 kg used in Example 4, so that the total amount of methanol, i.e., methanol mopped up from GL4+ methanol added equals approximately 64.5 kg (1.58 mole equivalent) used for the first lot of 370 kg. 344.8 kg of methyl ester was obtained in the first step having 0.075% total glycerol and 0.01% free glycerol and 339 kg of methyl ester was obtained in the next stage having 0.17% total glycerol and 0.02% free glycerol. This example teaches us the actual reduction in methanol usage in addition to the gains from avoiding methanol distillation. Since methanol would once again be recovered from the crude glycerol layer, the net usage of methanol is 1.22 equivalents with respect to methyl ester without any recovery through distillation, which works out 2.66 kg unrecoverable methanol per 100 kg of refined methyl ester produced.

EXAMPLE 7

As can be seen from Example 4 above, the glycerol washing of methyl ester layer removes the KOH catalyst very efficiently. It may therefore be advantageous to remove the traces of residual alkali metal impurities by ion exchange method which would obviate the need for water wash.

1. Preparation of macroporous cation exchange resin: Styrene-divinylbenzene (Styrene-DVB) copolymers with porous structures were prepared by suspension polymerization using cetyl alcohol as porosogenic agent. The copolymerization process was run in a 1-L three-necked round bottom flask fitted with a variable-speed mechanical stirrer, a thermometer and a reflux condenser. The monomer phase containing styrene 66 ml, DVB 18.5 ml and cetyl alcohol (70 g) with the initiator (benzoyl peroxide; 1% by weight of monomers) was poured into the reactor containing the aqueous solution of suspending medium. The suspension agent used in the synthesis was hydroxy ethyl cellulose (0.6 g), sodium lignosulfonate (0.6 g) and calcium chloride (5.3 g) in 420 ml water. The polymerization was carried out at 80±5° C. for 3 h and at 90±5° C. for further 3 h. The copolymer was obtained in the form of beads. These beads were then separated, washed and dried and solvent extracted to remove the porosogenic agent. The above synthesized co-polymer beads were subjected to sulfonation to introduce —$SO_3^-$ $H^+$ groups in the co-polymer matrix. The volume ratio of the co-polymer to the sulfuric acid used in sulfonation was 1:7. The reaction was carried out at 95±5° C. for 10 hours. The surface area by p-nitrophenol adsorption method was found to be 104.3 $m^2/g$. The cation-exchange capacity under dynamic condition was 1.8-2.1 meq/ml and 4.5 to 5.0 meq/g under static condition.

2. Purification of crude *Jatropha* methyl ester: The macroporous resin was loaded into a glass column having 4.6 cm internal diameter and 110 cm height. The column had stop-cock with glass wool plug in the bottom and B-24 joint at the top. The resin bed height was 65 cm and resin bed volume was 1.08 L. The resin bed was made moisture free by passing methanol. The glycerol-washed methyl ester layer (JME-$G_3$W) of example 3 was passed over the resin bed at a service flow rate of 5 bed volumes/hour. The effluent fractions of 10 L each were collected separately and the results obtained are presented in Table 3 below. It can be seen that the [$Na^+$] and [$K^+$] level reduces from 21.37 mg/L to 0.42 mg/L which satisfies the standard specifications for methyl ester. The moisture and methanol can both be eliminated through sparging with dry air. The first 10 L of methyl pester which contain higher amounts of MeOH after passing through resin can be recycled in the transesterification process. Other adsorbents reported in the prior art can be additionally taken in a separate column to reduce other impurities besides alkali metal ion.

EXAMPLE 8

Methanol Estimation in Methyl Ester and Crude Glycerol Layers for the Experiments of Examples 5-7

Figure 2:
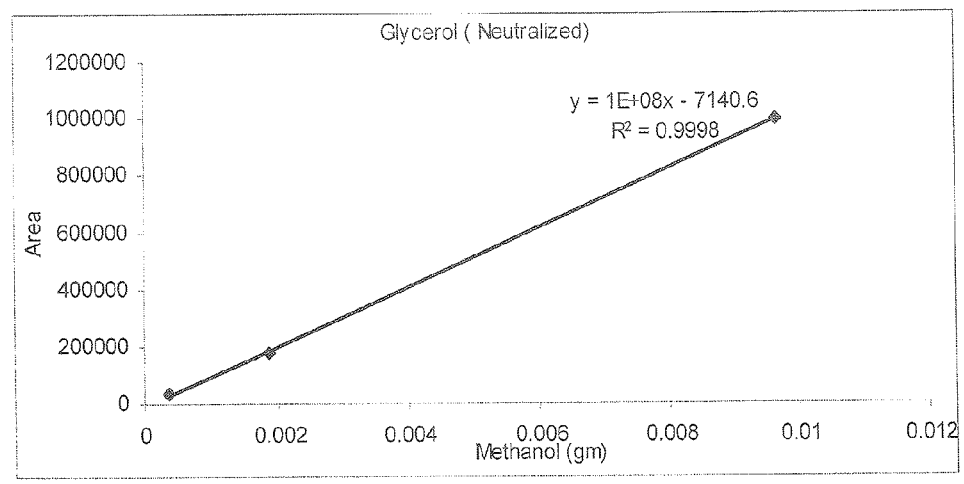
FIG. 2 represents the calibration plot of methanol content in glycerol employed for the estimation of methanol in crude glycerol layers (Examples 5-8, wherein Example 8 describes the analytical methodology).
Figure 3:
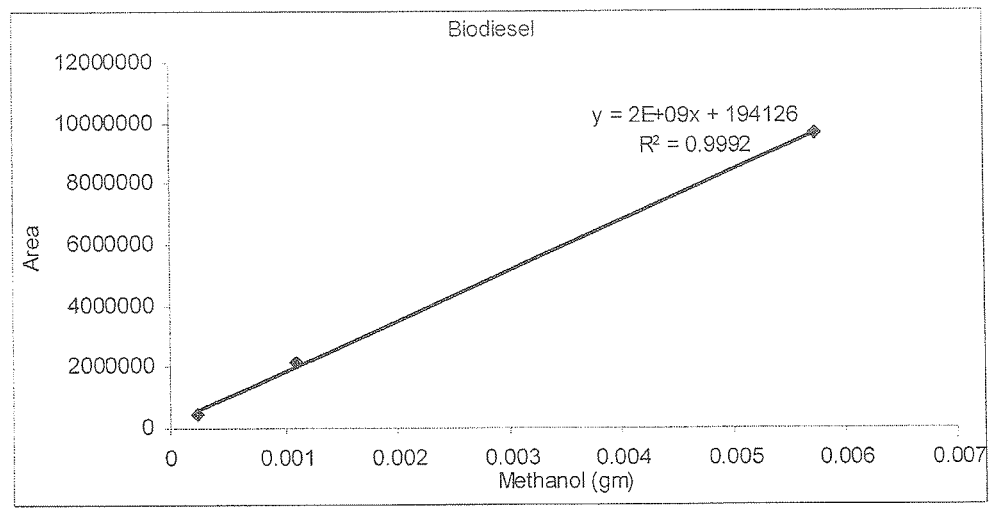
FIG. 3 represents the calibration plot of methanol content in methyl ester (Examples 5-8, wherein Example 8 describes the analytical methodology).

Standards were prepared using serial dilution of stock solution (10.0% w/w) which itself was prepared as follows: 18 g KOH and 50 g MeOH were added into a stoppered flask. 13.76 g of the methanolic KOH was diluted to 100 g with glycerol (A). 10 g of (A) was thereafter diluted to 100 g with glycerol (B). The stock solution was then diluted with water to yield the standard solutions. For sample preparation, 1.0 g of sample and 1.0 mL of 0.13 N glacial acetic acid were taken in a stoppered flask and diluted to 100.0 g with double distilled water GC-MS analysis of methanol content was performed using Shimadzu QP 2010 gas chromatograph mass spectrometer, equipped with headspace analyzer (AOC 5000 auto injector). HP PLOT U fused silica capillary column (0.53 mm ID×30 m Length×20 um film thickness) was used with helium as the carrier gas (at 1 mL/min flow rate). The column temperature was held at 100° C. for 10 min (isothermal). The mass spectrometer was operated at electron ionization energy of 70 eV. 1 ml of sample/standard was kept in air tight closed glass vial and kept in auto injector. Sample was heated at 65° C. and rotated for 5 min in incubator. 250 ul of gas was injected in split-split less injector which was at 150° C. The calibration plot drawn with the three standards had a regression coefficient ($R^2$) 0.9998 (FIG. 2). Similar calibration plot was made for MeOH in methyl ester (FIG. 3).

EXAMPLE 9

Estimation of Total K and Alkalinity in Crude Glycerol Layers and Methyl Ester for the Experiments of Examples 5-7

For water soluble samples, known weight of sample was dissolved to obtain fixed volume of aqueous solution whereas for insoluble samples, known weight of sample was washed with known volume of distilled water to extract the potassium hydroxide/salts into water. These samples were then analysed by flame photometry for total K after due calibration. Alkalinity was estimated through acid-base titration (Table 3).

EXAMPLE 10

Estimation of Traces of K and Na in *Jatropha* Methyl Ester Employing Ion Exchange Chromatography for the Experiments of Examples 4-7

The concentrations of sodium and potassium cations in the biodiesel water washes were determined by ion exchange

TABLE 3

Figure 4:
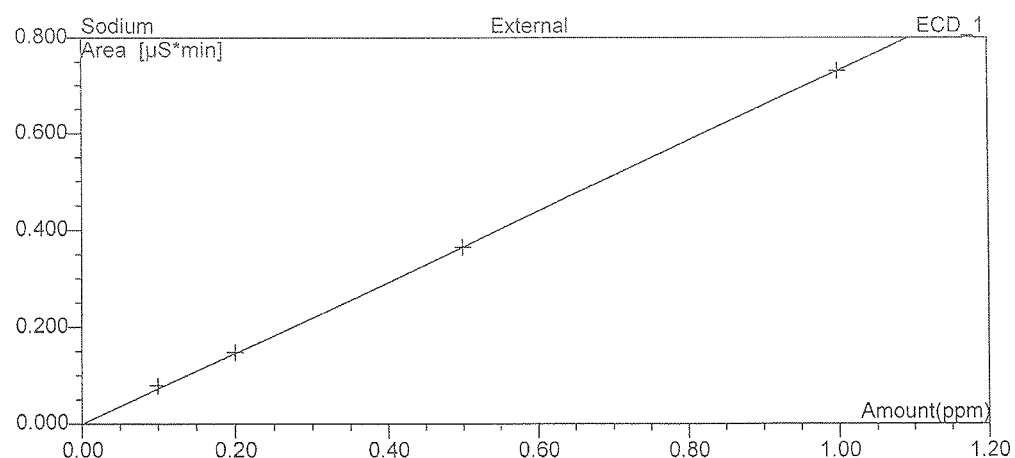
FIG. 4 represents the calibration plot for traces of sodium in methyl ester (Examples 7 & 10, wherein the latter describes the analytical methodology).
Figure 5:
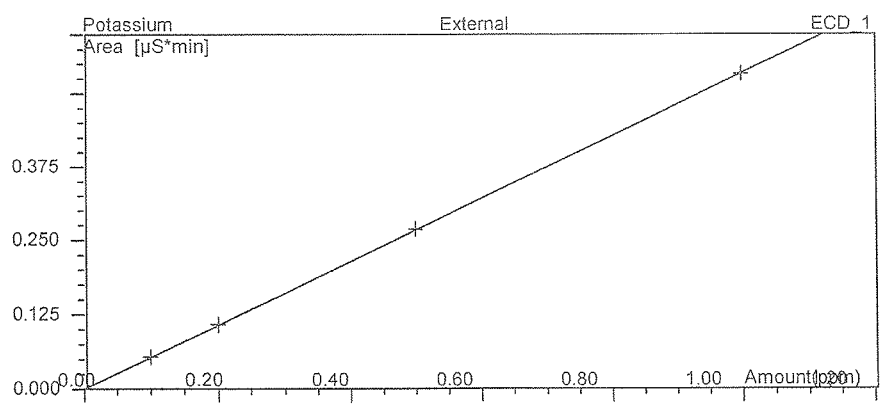
FIG. 5 represents the calibration plot for traces of potassium in methyl ester (Examples 7 &. 10, wherein the latter describes the analytical methodology).

| Amount Treated by the resin/L | $Na^+$ (mg/L) | $K^+$ (mg/L) | [$Na^+$ + $K^+$] (mg/L) | MeOH (% w/w) | $H_2O$ % | Total glycerol/ (free glycerol) % w/v/ (% w/v) | FFA (% w/w) | Turbidity (NTU) |
|---|---|---|---|---|---|---|---|---|
| Influent | 5.07 | 16.3 | 21.37 | 0.6071 | 0.0984 | 0.30(0.03) | 0.1827 | 0.30 |
| 0-10 L | 0.31 | 0.89 | 1.20 | 2.6344 | 0.1742 | 0.40(0.01) | 0.183 | 0.3 |
| 10-20 L | 0.31 | 0.11 | 0.42 | 0.7831 | 0.1502 | 0.43(0.01) | 0.183 | 0.31 |
| 20-30 L | 0.27 | 0.15 | 0.42 | 0.8849 | — | — | — | 0.16 | chromatography with conductivity detector using Ion Pac CS12 (2 mm) analytical column and 20 mM methane sulphonic acid as eluant with a flow rate of 0.25 mL/min. Quantification was made using standard solutions containing a mixture of NaCl and KBr (0.1, 0.2, 0.5 and 1.0 ppm each). The relative standard deviation, correlation coefficient and slopes were (1.0191, 1.0000 and 0.7313 for sodium and 0.6605, 1.0000 and 0.5341 for potassium), respectively. The calibration plots for sodium and potassium as well as the chromatograms of samples are given in FIGS. 4 and 5.

EXAMPLE 11

The spent glycerol layer, GL 7, of Example 4 was divided into two parts. One part was taken for neutralization of alkali with sulphuric acid, followed by separation of soapy matter and $K_2SO_4$ as per the process of the prior art. The purified glycerol layer was then subjected to distillation so as to recover the same amount of glycerol as required for the purpose of washing of methyl ester layer. The still bottom, having dark brown color (designated as GL8), was utilized as nutrient source for microbial production of polyhydroxyalkanoates (PHA) as described in example 12 below. The larger fraction of GL7 was utilized directly for preparation of PHA as described in example 13 below. *Jatropha* oil cake hydrolysate (JOCH) was extracted by treating *Jatropha* oil cake, having 4-6% (w/w) N, with hot acidic aqueous solution of $H_3PO_4/H_2SO_4$ and thereafter adjusting pH suitably with alkaline materials such as crude glycerol layer, potassium hydroxide and magnesium hydroxide to yield salts which have buffering action and also contribute to the nutrient value of the hydrolysate. Gram variable, Gram +ve (*Bacillus* sp., *Azotobacter* sp.) and Gram −ve bacteria (*Pseudomonas* sp.; *Halomonas* sp.) were isolated from soil and marine environment and screening for PHA production was done.

EXAMPLE 12

Example 12.1

30 soil bacterial isolates from Indian soil were screened in the lab for PHA production. Bacteria MTCC 5443 was found to be one of the most-efficient and has been used in the present invention. 100 ml of King's B growth medium was prepared comprising peptone 20 g, glycerol 15 g, dipotassium hydrogen phosphate 1.5 g and magnesium sulphate 1.5 g dissolved in one liter of distilled water. The medium was then autoclaved at 121° C. for 20 minutes. 1 ml of seed culture was inoculated in the above medium and incubated for 48 hours at 35+−2° C. in shaker. The culture was then harvested by centrifugation. 100 ml of a production medium was prepared containing 2% (w/v) GL8 of Example 11 above, 0.05 g $(NH_4)_2SO_4$, 0.04 g $MgSO_4 \cdot 7H_2O$, 0.965 g $Na_2HPO_4 \cdot 12H_2O$, 0.265 g $KH_2P)_4$ and 0.1 mL of a stock micronutrient solution containing $FeSO_4 \cdot 7H_2O$ (2.78 g/l), $MnCl_2 \cdot 4H_2O$ (1.98 g/l), $CoSO_4 \cdot 7H_2O$ (2.81 g/l), $CaCl_2 \cdot 2H_2O$ (1.47 g/l), $CuCl_2 \cdot 2H2O$ (0.17 g/l) and $ZnSO_4 \cdot 7H_2O$ (0.29 g/l) micronutrients in distilled water were added next into the medium. The medium was then autoclaved at 121° C. for 20 minutes. The harvested culture obtained from growth medium was then inoculated into the production medium and incubated on shaker (120 rpm) for 96 hours at 35+−5° C. The cells were harvested by centrifuging and the pellet obtained was oven dried to get cell dry weight of 0.38 g. The pellet was then treated with hypochlorite (4-6% chlorine) solution for 15 minutes to digest the cells. The solid polymer was recovered by centrifuging. It was then washed successively with water and methanol to remove adhering impurities and 0.27 g of PHA was obtained, amounting to 71.05% of cell dry weight.

These results may be compared with the results of Ashby et al. in the prior art wherein the PHA accumulation was found to be 42% of cell dry weight when co-product stream of soya-based biodiesel process was employed.

The above experiment was repeated with 2% (w/w) pure glycerol in production medium in place of 2% (w/w) GL8. As can be seen from Table 4 below, the yield of PHA with respect to cell dry weight was only 52.6% with pure glycerol compared to 71.1% with GL8. The carbon utilization efficiencies for PHA production were 11.45% and 20.8% for glycerol and GL8, respectively.

TABLE 4

| Parameters | GL8 (2%) | Pure Glycerol (2%) |
|---|---|---|
| Volume | 100 ml | 100 ml |
| Temperature | 35 ± C. | 35 ± C. |
| Wt. of sample taken | 2 g | 2 g |
| Carbon content in medium after autoclaving | 0.72 | 0.76 |
| Harvesting time | 90 hrs | 90 hrs |
| Cell dry weight | 0.38 g | 0.30 g |
| Yield of PHA | 0.270 g | 0.158 g |
| Yield of PHA based on Cell dry weight | 71.1% | 52.6% |
| Carbon content in PHA | 0.15 g | 0.087 g |
| % Carbon in medium which ends up in PHA | 20.8% | 11.45% |

The still bottom residue of Example 11, which is otherwise difficult to dispose off, yields PHA more efficiently than with even pure glycerol, presumably because the impurities act as promoters for PHA production. Details of metal impurities in GL7 and GL8 are provided in the Table 5 below.

TABLE 5

| ICP results of GL7 and GL8 | | |
|---|---|---|
| Analyte (mg/L) | GL7 | GL8 |
| Calcium | 3.263 | 8.189 |
| Cadmium | 0.002 | 0.002 |
| Cobalt | 0.000 | 0.002 |
| Chromium | 0.005 | 0.023 |
| Copper | 0.075 | 0.046 |
| Iron | 0.360 | 0.554 |
| Potassium | 48.90 | 21.63 |
| Magnesium | 2.183 | 3.552 |
| Manganese | 0.022 | 0.040 |
| Molybdenum | 0.004 | 0.004 |
| Sodium | 17.21 | 38.24 |
| Nickel | 0.006 | 0.022 |
| Lead | 0.015 | 0.152 |
| Zinc | 0.814 | 0.131 |

Figure 6:
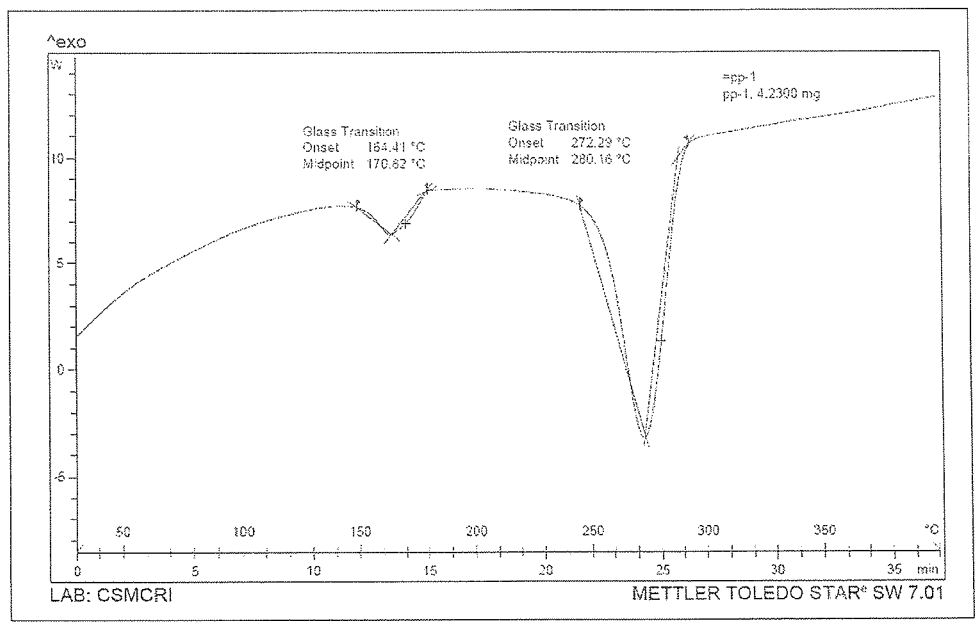
FIG. 6 represents the differential scanning calorimetric profile of PHA produced by the process of Example 12.1.

Characterization of Polyhydroxyalkanoates Obtained from GL8:

The PHA obtained using GL8 was found to have a polydispersity index ($M_w/M_n$) of 1.4640, with $M_w$ and $M_n$ values of 35990 and 24583, respectively. The proton and $^{13}C$ NMR matched that of standard PHA (from Sigma). However, the melting point by DSC was 166.2° C. (narrow) (FIG. 6) compared to a value of 146.9° C. (broad) for standard PHA. (All of the above data on polymer physical properties are courtesy Solvay Specialties India Private Limited.) Films made from the polymer of the present invention were measured for load carrying capacity. The load carrying capacity was found to be 7-8 psi for a film of 40.5 mm diameter and 0.05 mm thickness.

The films, in turn, could be converted into capsules, pouches and were amenable to heat sealing. These films showed evidence of bio-degradation after 50 days when buried in moist garden soil. Tougher films could be made by increasing the film thickness or by blending PHA of the present invention with polymethylmethacrylate.

Example 12.2

The experiment of Example 12.1 was repeated in identical manner except for the following changes in the production medium: (i) 2% GL8 was replaced with 2% GL7 and the pH of the medium was made neutral with 85% H3P04 prior to inoculation of culture, (the medium after addition of GL7 was sparged to eliminate residual methanol in GL7 (note that, unless otherwise mentioned, wherever GL7 was used such sparging was resorted to), and (ii) $Na_2HPO_4.12H_2O$ and $KH_2PO_4$ added in the production medium of Example 12.1 were excluded. PHA content was found to be 49.3% (w/w) of cell dry weight compared to 71.1% with GL8. Thus, the MTCC-5443 culture may not respond identically when there are variations in the compositions of the crude glycerol fractions.

Example 12.3

Since King's B medium is expensive, and further since the medium contains peptone and glycerol, the experiment of Example 12.1 was repeated in identical manner except that the King's B growth medium was replaced with 10% (v/v) *Jatropha* oil cake hydrolysate (JOCH) and 2% (w/v) GL7, the former providing nitrogen as amino acid and the latter providing glycerol. However, when the culture grown in the above growth medium was inoculated in the production medium of Example 12.2, the PHA yield was found to be further reduced to 28.2% (w/w) of cell dry weight.

Even though King's B medium can, in principle, be replaced with more cost effective medium derived from by-products of the biodiesel process itself, the substitution adversely affects the yield of PHA with respect to cell dry weight in case of MTCC-5443.

EXAMPLE 13

Example 13.1

The experiment of Example 12.2 was repeated using a marine bacteria isolated from Aadri (Latitude 20°57.584', Longitude 70°16.759'), Veraval coast of Gujarat India (MTCC 5445) having 99.63% sequence identity with *Halomonas hydrothermalis*. This bacteria was screened from among 60 marine bacteria and found to yield higher quantity of PHA. The King's B growth medium was substituted with Zobell's marine medium comprising: peptone 5.0 g, yeast extract 1.0 g, ferric citrate 0.1 g, sodium chloride 19.45 g, magnesium chloride 8.8 g, sodium sulfate 3.24 g, calcium chloride 1.8 g, potassium chloride 0.55 g, sodium bicarbonate 0.16 g, potassium bromide 0.08 g, strontium chloride 34.0 mg, boric acid 22.0 mg, sodium silicate 4.0 mg, sodium fluoride 2.4 mg, ammonium nitrate 1.6 mg and disodium phosphate 8.0 mg in one liter of the medium maintained at pH 7.6±0.2. The marine bacteria was cultured in this broth to obtain seed culture having O.D. of 1.7-1.9. The centrifuged biomass was inoculated in the production medium which was the same as in Example 12.2. The yield of PHA with respect to cell dry weight was 71.2% (w/w).

It was found that the use of GL7 for production of PHA is more effective with the marine bacteria MTCC 5445 isolated in the course of the present invention than the MTCC 5443 isolated from soil.

Example 13.2

The experiment of Example 13.1 with marine bacteria (MTCC 5445) was repeated except that the Zobell's marine growth medium was replaced with 10% (v/v) JOCH and 2% (w/v) GL7. The yield of PHA with respect to cell dry weight was 69.8% (w/w), i.e., almost identical to that in Example 13.1 above. The percent of carbon in the medium which ended up in PHA was 11.30% (w/w). Details of the experimental data are provided in the Table 6 below.

TABLE 6

| Stage 1 fermentation—Growth | |
|---|---|
| JOCH | 10 mL |
| GL7 | 2 g |
| Neutralizing acid | 85% $H_3PO_4$ |
| pH | 7.2 |
| Seed culture (grown in Zobell's marine medium) | 1 mL |
| Total volume of growth medium | 100 mL |
| Temperature of growth medium | 35 ± 2° C. |
| Duration of growth | 48 h |
| Stage 2 fermentation—PHA Production | |
| GL7 | 2 g |
| Inoculum | Total culture harvested from the growth medium |
| Ammonium sulphate | 0.05 g |
| Magnesium sulphate | 0.04 g |
| Micronutrient solution (see Example 6) | 0.1 mL |
| Total volume | 100 mL |
| Temperature | 35 ± 2° C. |
| Carbon amount in culture medium | 0.69 g |
| pH | 7.00 |
| Incubation time | 96 hours |
| Cell dry weight | 0.20 g |
| Yield of PHA based on cell dry weight | 69.8% |
| Absolute yield of PHA | 0.1396 g |
| Weight of C in PHA obtained (55.58% carbon content by CHN—S elemental analysis) | 0.078 g |
| % of carbon consumed in fermentation process which ends up in PHA | 11.30% |

Example 13.3

Figure 7:
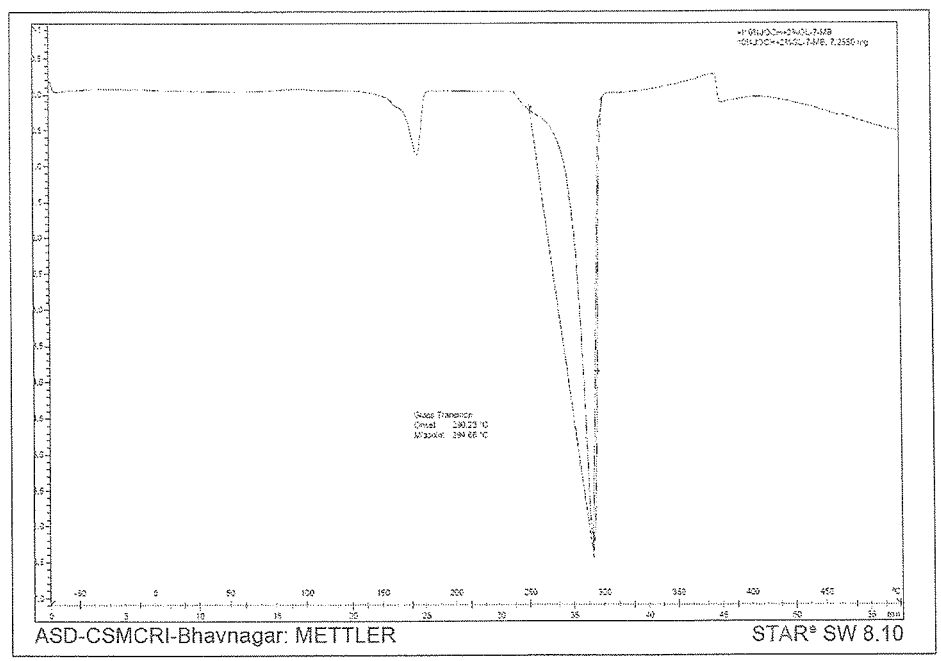
FIG. 7 represents the differential scanning calorimetric profile of PHA produced by the process of Example 13.3.

The experiment of Example 13.2 with marine bacteria (MTCC 5445) was repeated with the following simplifications: (i) growth and production stages were combined into a single stage, (ii) other than GL7 and JOCH no other nutrients/micronutrients were provided, (iii) pH was allowed to self adjust (it became 7.7) through internal neutralization between GL7 and JOCH and, as such, no deliberate adjustment was made of pH, (iv) no sparging was carried out for removal of methanol in GL7 and the incubation was carried out under ambient temperature conditions which varied from 28[deg.] C. at night/early morning to 37[deg.] C. during noon time. 1-10% (v/v) of seed culture was directly inoculated into 100 mL of a growth-cum-production medium containing 2-10% (w/v) of the crude glycerol of step (xiii) and 5-20% (v/v) of *Jatropha* oil cake hydrolysate as prepared in example 3. As can be seen from Table 7 below, PHA production was 75.1% (w/w) with respect to cell dry weight. The absolute weight of PHA was 89% higher than in Example 13.2 while the percentage of carbon in the medium which ended up in PHA after 96 h of incubation was also higher at 18.8%. The DSC melting point of the purified PHA was 172[deg.] C. (FIG. 7). Thus simplification of methodology (complete avoidance of work up of GL7; single stage fermentation; time saving; ambient condition processing) together with greater cost-effectiveness (nutrients provided only by GL7 and JOCH co-product streams of *Jatropha* methyl ester process; energy saving) while, at the same time, raising the efficiency of PHA production are demonstrated through this example.

TABLE 7

Single stage PHA production

| | |
|---|---|
| JOCH | 10 mL |
| GL7 | 2.00 g |
| pH | 7.7 |
| Total volume | 100 mL |
| Carbon content in medium after autoclaving | 0.78 g |
| Nitrogen content in medium after autoclaving | 0.097 g |
| Temperature of growth medium | 28-37° C. |
| Seed culture (grown in Zobell's marine medium) | 1 mL |
| Incubation time | 96 hours |
| Cell dry weight | 0.353 g |
| Weight of PHA isolated | 0.265 g |
| Yield of PHA based on cell dry weight | 75.1% |
| Carbon content of PHA produced (@55.58% w/w) | 0.147 g |
| % of carbon in medium which ends up in PHA | 18.8% |

Example 13.4

The experiment of Example 13.3 was conducted with 4 L of fermentation broth taken in a 5 L flask which was left under ambient conditions in a shaker. The wet biomass harvested after 96 h weighed 39 g, the yield of dry biomass was 5.57 g, and the yield of PHA was 4.3 g (77% PHA with respect to cell dry weight).

Example 13.5

The experiment of Example 13.3 was repeated except that 2 g GL7 was replaced with 2 g of 9:1 mixture of GL7 and GL8 and the incubation time was one week. The yield of dry biomass harvested was 0.615 g while the yield of PHA was 0.425 g, i.e., the PHA yield was 69% (w/w) with respect to cell dry weight and 30.2% with respect to carbon content in the medium.

Example 13.6

Some of the PHA samples obtained from examples 11 to 13.5 were dissolved in chloroform and fabricated into films by casting on clean, dry, glass plates and the chloroform was evaporated slowly. PHA film was prepared by dissolving 0.5 to 5% of PHA in chloroform (w/v). The films were air dried; complete evaporation resulted in formation of films. The film thickness was 0.016-0.28 mm as measured by micrometer. Films buried in the moist garden soil were found to biodegrade after 50 days.

Advantages of the Invention

1. Utilization of co-streams for preparation of high density energy briquettes and Polyhydroxyalkanoate biodegradable polymer in efficient and cost-effective manner.
2. The glycerol washing process to purify the methyl ester leaves very little of the methanol in the methyl ester, instead, it is confined to the extent of 90-95% in the glycerol layer.
   methyl ester can be treated with small bed volumes of resin without regeneration.

We claim:

1. A process for the preparation of *Jatropha* Methyl Ester and byproducts comprising the steps of:
   (a) expelling oil, oil cake and waste oil sludge from *Jatropha* seeds;
   (b) neutralizing the *Jatropha* oil to lower a free fatty acid content of the *Jatropha* oil;
   (c) transesterifying a first portion of the *Jatropha* oil neutralized in step (b) with an alcohol and a base as catalyst with stirring to form a crude *Jatropha* methyl ester layer and a crude glycerol layer, each of the crude *Jatropha* methyl ester layer and the crude glycerol layer comprising unreacted alcohol and partly active catalyst, and separating the crude glycerol layer and crude *Jatropha* methyl ester layer;
   (d) washing the crude *Jatropha* methyl ester layer separated in step (c) a plurality of times with glycerol and recovering a first portion of *Jatropha* methyl ester and a plurality of impure glycerol layers containing unreacted alcohol and partly active catalyst;
   (e) treating a second portion of the *Jatropha* oil neutralized in step (c) with the crude glycerol layer and first and second of the plurality of impure glycerol layers with stirring to transesterify the second portion of the *Jatropha* oil to form a second *Jatropha* methyl ester layer and a further glycerol layer, and separating the second *Jatropha* methyl ester layer and the further glycerol layer;
   (f) treating a third portion of the *Jatropha* oil neutralized in step (c) with the further glycerol layer with stirring to transesterify the third portion of the *Jatropha* oil, separating a third *Jatropha* methyl ester layer and a spent glycerol layer and, optionally, treating the recovered third *Jatropha* methyl ester layer with additional amounts of the alcohol and base and washing with glycerol; and
   (g) optionally treating a further portion of *Jatropha* oil neutralized in step (c) with the crude glycerol layer and the plurality of impure glycerol layers;
   wherein, in steps (e)-(g), unreacted alcohol in the respective crude glycerol layer, the first and second impure glycerol layers and the further glycerol layer are reactants in the transesterifying of at least the respective second and third portions of the *Jatropha* oil resulting in depletion, without distillation, of 80-95% of the unreacted alcohol that was present in the crude glycerol layer separated in step (c), wherein a portion of the spent glycerol layer is incorporated into a bacterial culture medium for production of polyhydroxyalkanoates, and wherein the process further comprises treating the oil cake with acid, recovering a hydrolysate, incorporating the hydrolysate into the bacterial culture medium as a nutrient and inoculating the bacterial culture medium with marine bacteria comprising MTCC 5445.

2. The process according to claim 1, wherein the process further comprises incubating the bacterial culture medium with the marine bacteria for a period of 24-96 hours at a pH of 7-8 and a temperature in a range of 25-40° C. to allow fermentation and to obtain a fermented product, harvesting pellets from the fermented product by centrifugation, recovering solid polymer by centrifugation of the pellets, washing the solid polymer with water and methanol to obtain polyhydroxyalkanoates (PHA).

3. The process according to claim 2, wherein the PHA yield with respect to cell dry weight is in a range of 69% to 77%.

4. The process according to claim 3, wherein the PHA has a melting point determined by differential scanning calorimetry of 166.2° C. and polydispersity index values for $M_w$, $M_n$, and $M_w/M_n$ of 35990, 24583 and 1.46 respectively.

5. The process according to claim 2, further comprising dissolving the PHA in chloroform to obtain a PHA film.

6. The process according to claim 1, wherein the first portion of *Jatropha* methyl ester recovered in step (c) comprises no more than 10% of the unreacted alcohol and is purified with an ion exchange resin to remove alkali metal impurities without a water wash.

7. The process according to claim 1, wherein the *Jatropha* seeds from which oil, oil cake and waste oil sludge are expelled in step (a) are obtained by mechanically de-shelling seeds of *Jatropha* that are naturally encapsulated in a capsule to obtain the *Jatropha* seeds and *Jatropha* shells, the mechanical de-shelling being performed sufficiently close to when the expelling in step (a) is performed so that the *Jatropha* seeds have a free fatty acid value of 0.5 to 2.0% at the time of the expelling.

8. The process according to claim 7, comprising briquetting the *Jatropha* shells in a briquetting machine with addition of the waste oil sludge to obtain *Jatropha* briquettes with a density of 1.05-1.110 g/cm$^3$.

9. The process according to claim 8, wherein the de-shelling is performed by breaking the shells open by impact against a stationary surface, separating the seeds from the shells by vibration along a sloping sieve surface, and blowing off the separated shells.

10. The process according to claim 1, wherein the base is selected from the group consisting of potassium hydroxide and sodium hydroxide.

11. The process according to claim 1, wherein the alcohol is selected from the group consisting of methanol and ethanol.

12. The process according to claim 1, comprising combining the purified first portion of *Jatropha* methyl ester with a second portion of *Jatropha* methyl ester from the second *Jatropha* methyl ester layer and with a third portion of *Jatropha* methyl ester from the third *Jatropha* methyl ester layer, and transesterifying the combined first, second and third portions of *Jatropha* methyl ester with methanolic KOH.

\* \* \* \* \*